United States Patent
Hsieh

(12) 
(10) Patent No.: US 6,236,706 B1
(45) Date of Patent: May 22, 2001

(54) METHODS AND APPARATUS FOR PREDICTING CONTRAST AGENT UPTAKE IN A COMPUTED TOMOGRAPHY SYSTEM

(75) Inventor: Jiang Hsieh, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/521,292

(22) Filed: Dec. 12, 1996

(51) Int. Cl.⁷ ........................................... A61B 6/03
(52) U.S. Cl. .................. 378/8; 378/15; 378/901
(58) Field of Search ............... 378/4, 8, 15, 18, 378/98.12, 901

(56) References Cited

U.S. PATENT DOCUMENTS

| | | | |
|---|---|---|---|
| 5,459,769 | 10/1995 | Brown | 378/4 |
| 6,001,333 | * 12/1999 | See | 424/9.4 |

* cited by examiner

Primary Examiner—David V. Bruce
(74) Attorney, Agent, or Firm—Armstrong Teasdale LLP; Christian G. Cabou

(57) ABSTRACT

The present invention, in one form, is a system which predicts contrast agent uptake in an organ of interest. In accordance with one embodiment, and after the contrast agent has been administered to a patient, a prep scan is performed to determine a base contrast agent uptake measurement. A predictive algorithm is then applied to the base measurement to predict a subsequent contrast agent uptake measurement. The predicted subsequent measurement is then compared to a scanning parameter. Particularly, if the predicted subsequent measurement satisfies the scanning parameter, then an image scan is initiated. If the predicted subsequent measurement does not satisfy the scanning parameter, however, then an additional prep scan is performed to determine a new base contrast agent uptake measurement. The predictive algorithm is then applied to the new base measurement to predict a subsequent contrast agent uptake measurement. The prep scans and predictions are repeated until the predicted subsequent contrast agent uptake measurement satisfies the scanning parameter.

16 Claims, 3 Drawing Sheets

METHODS AND APPARATUS FOR PREDICTING CONTRAST AGENT UPTAKE IN A COMPUTED TOMOGRAPHY SYSTEM

FIELD OF THE INVENTION

This invention relates generally to computed tomography (CT) imaging and more particularly, to predicting contrast agent uptake in a patient before performing a computed tomography scan.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

When performing computed tomography imaging, contrast agents typically are used to enhance image contrast, i.e., to "highlight" an organ of interest from surrounding tissue. Particularly, and with respect to a region of interest, a contrast agent is administered to a patient and the contrast agent is more greatly absorbed by the region of interest than by the other tissues. To obtain images maximizing the contrast between the region of interest and the surrounding tissue, it is preferable to perform a scan during peak contrast agent uptake.

Known methods for attempting to obtain scan data during peak contrast agent uptake in a patient typically require continuously performing low intensity scans, or prep scans, of the region of interest until the scan operator determines that the contrast agent uptake is adequate. After determining that the contrast agent uptake is adequate, the operator initiates the image scan, i.e., a full helical scan.

The known contrast uptake determination methods depend upon the experience of the operator and, particularly with less experienced operators, may result in sub-optimal scans. For example, because of an inherent lag in the CT reconstruction process, images reconstructed using data obtained in a prep scan do not represent the actual state of the contrast uptake when the last view was acquired. Rather, such images represent an averaged contrast uptake during the data acquisition period. Accordingly, at a particular time, the contrast agent uptake may be higher than represented by the prep scan image.

In addition, a considerable delay occurs between initiating the image scan and actually performing the image scan. Specifically, and before performing the scan, the patient must be positioned so that the entire organ volume can be covered, the x-ray tube current level must be increased to the appropriate scanning intensity, and the patient must perform a breath hold. Positioning the patient and increasing the x-ray tube current level typically take several seconds. Similarly, patients typically require several additional seconds to begin a long breath hold.

These delays can result in sub-optimal image scans. Since the contrast agent uptake peaks and diminishes within a significantly short period of time (e.g., 10–30 seconds), the image scan may be performed at a time other than at the time of peak contrast agent uptake.

It would be desirable to perform an image scan during peak contrast agent uptake despite the delays inherent in the scanning process. It also would be desirable to perform such a scan without significantly increasing the costs of known CT systems.

SUMMARY OF THE INVENTION

These and other objects may be attained by a system which, in one embodiment, predicts contrast agent uptake in an organ of interest. More particularly, and in accordance with one embodiment, a prep scan is performed to determine at least one base contrast agent uptake measurement, and a predictive algorithm is applied to the base measurement to predict at least one subsequent contrast agent uptake measurement. If the predicted subsequent measurement satisfies a scanning parameter, then an image scan is initiated so that even with the delays described above, the image scan is performed approximately during the contrast agent uptake peak.

If the predicted subsequent measurement does not satisfy the scanning parameter, then an additional prep scan is performed to determine a new base contrast agent uptake measurement. The predictive algorithm is then applied to the new base measurement to predict a subsequent contrast agent uptake measurement. In addition, the predictive algorithm may be dynamically adjusted using the previous contrast agent uptake measurements to improve the accuracy of the predictions. The prep scans and predictions are repeated until the predicted subsequent contrast agent uptake measurement satisfies the scanning parameter.

The system described above substantially overcomes the difficulties associated with performing a scan during peak contrast agent uptake due to CT system scanning delays, and facilitates performing image scans during peak contrast agent uptake. In addition, such system is inexpensive to implement in connection with known CT systems.

DETAILED DESCRIPTION OF THE DRAWINGS

Figure 1:
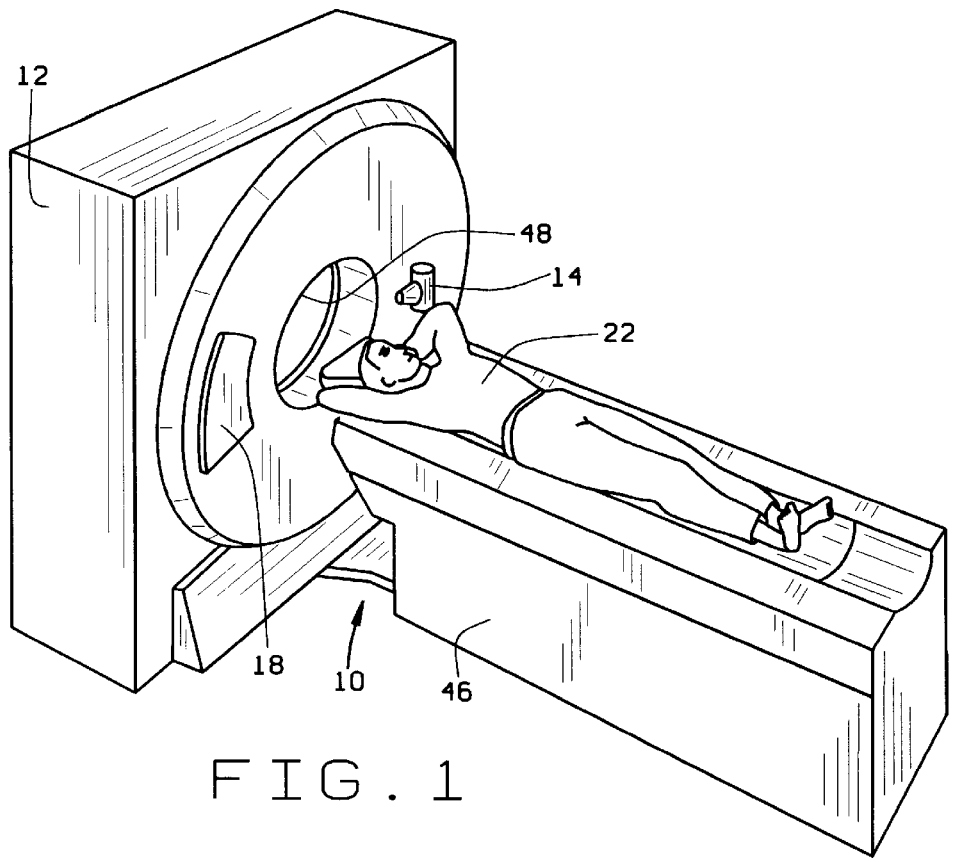
FIG. 1 is a pictorial view of a CT imaging system.
Figure 2:
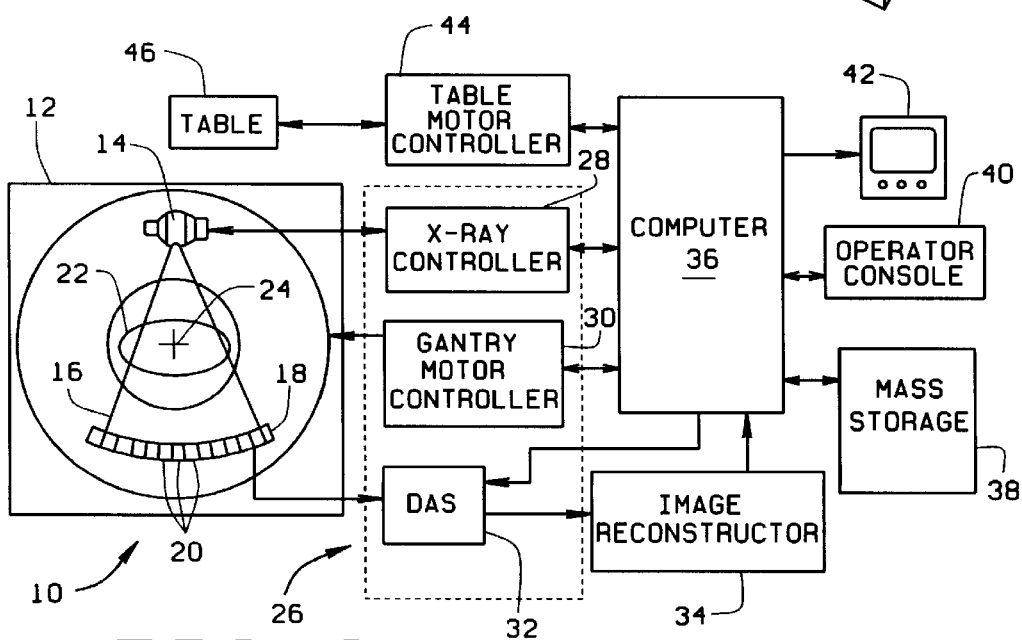
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. X-ray beam 16 is collimated by a collimate (not shown) to lie within in an X-Y plane of a Cartesian coordinate system and generally referred to as an "imaging plane". Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion relates to methods and apparatus for predicting contrast agent uptake in patient 22, and more particularly, in an organ of interest of patient 22. Although such methods and apparatus sometimes are described in the context of CT system 10, it should be understood that such methods and apparatus are not limited to practice or use in connection with only CT system 10. It should be further understood that the predictive algorithm discussed herein would be implemented in computer 36 and would process, for example, scan data stored in mass storage 38. Other alternative implementations are, of course, possible.

Figure 3:
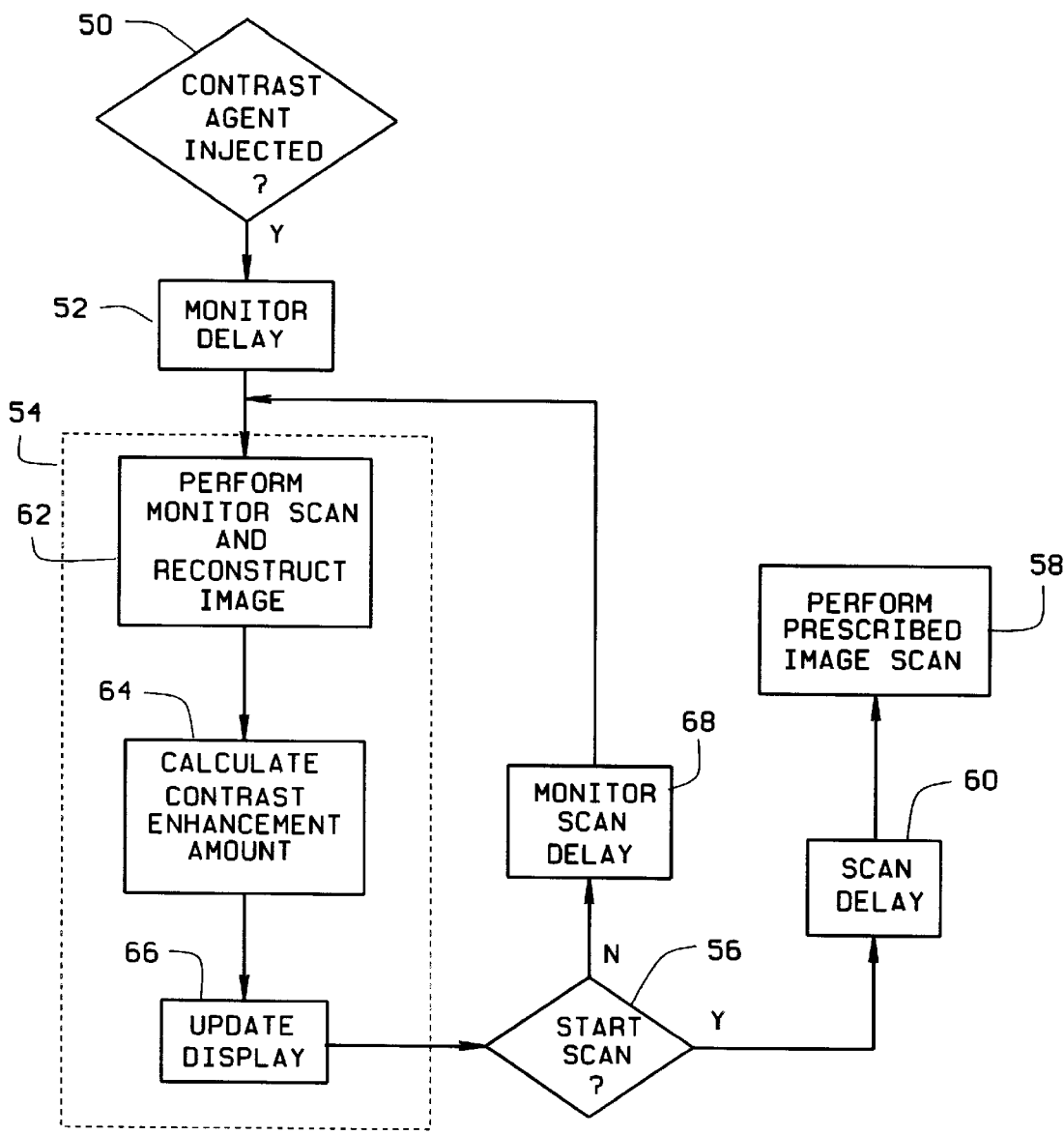
FIG. 3 is a flow chart illustrating a sequence of process steps in accordance with a known algorithm used in an attempt to obtain scan data during the peak contrast agent uptake.

FIG. 3 is a flow chart illustrating a sequence of process steps in accordance with a known algorithm used in an attempt to obtain scan data during the peak contrast agent uptake. Particularly, after the patient has been injected 50, and after a monitor delay 52, contrast agent uptake is measured 54. If the contrast agent uptake exceeds a scanning threshold level, then an image scan is initiated 56. However, the image scan is performed 58 only after a scan delay 60. The scan delay, as described above, includes time required for the positioning patient so that the entire volume of the organ of interest can be imaged, for increasing x-ray tube current level to an appropriate scanning intensity, and for waiting for the patient to perform a breath hold.

Measuring contrast agent uptake 54 includes performing a monitor scan and reconstructing an image in accordance with the data acquired for such scan 62. The data also is used to calculate a contrast enhancement amount 64, i.e., to determine a contrast uptake measurement. The contrast enhancement amount is then displayed 66 and compared to the scanning threshold level to determine whether to initiate the image scan 56. If the contrast enhancement amount does not exceed the scanning threshold, then a monitor scan is again performed 62 after a monitor scan delay 68.

As shown in FIG. 3, a scan delay 60 occurs between initiating the image scan 56 and performing the image scan 58. Scan delay 60, as described above, typically causes sub-optimal image scans. Particularly, and since contrast agent uptake peaks and diminishes within a significantly short period of time, i.e., 10–30 seconds, the image scan may actually be performed at a time other than at the peak contrast agent uptake. Furthermore, by the time the image scan is completed, a significant portion of the contrast agent may have already been expelled from the organ of interest. Accordingly, it would be desirable to perform the image scan at approximately the same time the contrast agent uptake measurement peaks.

Figure 4:
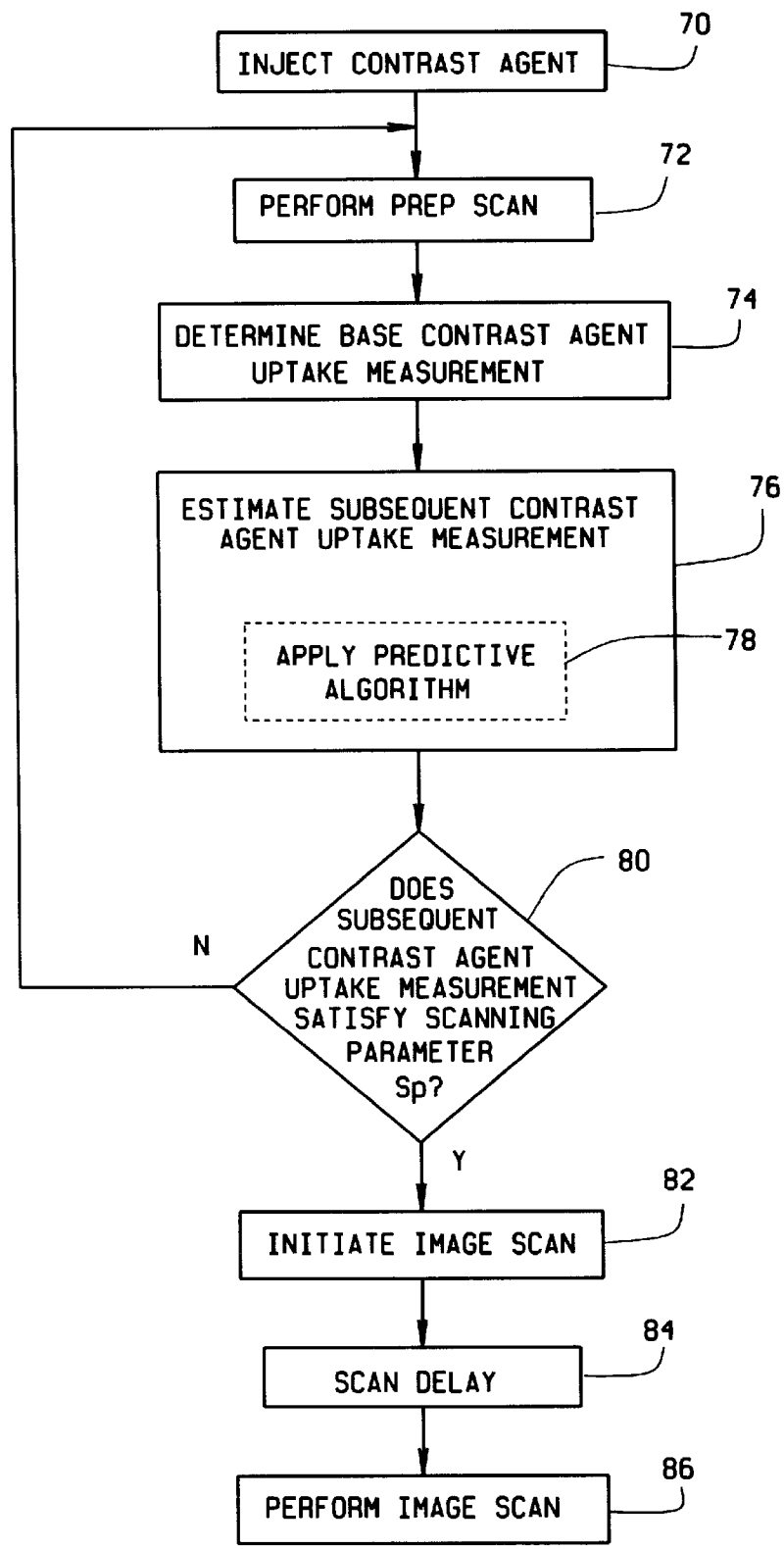
FIG. 4 is a flow chart illustrating a sequence of process steps in accordance with one embodiment of the present invention for predicting contrast agent uptake in an organ of interest.

FIG. 4 is a flow chart illustrating a sequence of process steps in accordance with one embodiment of the present invention for predicting contrast agent uptake in an organ of interest. Particularly, and after patient 22 has been injected with a contrast agent 70, a prep scan is performed 72 and a base contrast agent uptake measurement, $M_{B1}$, is determined 74. Injecting a contrast agent into patient 22 is well known. Similarly, performing prep scans to obtain contrast agent uptake measurements are well known. Typically, the prep scans are performed with low x-ray tube current and the contrast agent uptake measurements are determined in accordance with the CT numbers generated from data acquired during the prep scan.

After determining base contrast agent uptake measurement, $M_{B1}$, a subsequent contrast agent uptake measurement, $M_{Supp1}$, is predicted 76. Particularly, a predictive algorithm is applied 78 to base contrast agent uptake measurement, $M_{B1}$, to predict subsequent contrast agent uptake measurement, $M_{Supp1}$, at a time, t, in the future. Predictive algorithms which can be used for making the above described prediction are well known, and one such predictive algorithm is described, for example, in John J. Westerkamp, "Adaptive Signal Processing" (IEEE product no. HV0092-7 (1989)). As also is known, predictive algorithms may include a priori knowledge of patient 22 and the contrast agent to facilitate the accuracy of contrast agent uptake predictions. Specifically, a predictive algorithm may include parameters utilizing physiological characteristics such as patient age, sex, height and weight, the precise organ being scanned, and the type of contrast agent injected into patient 22. Time, t, typically is selected to be the current time plus the time required to initiate a scan.

Predicted contrast agent uptake measurement, $M_{Supp1}$, is then compared 80 to a scanning parameter, $S_p$. If predicted subsequent contrast agent uptake measurement, $M_{Supp1}$, satisfies scanning parameter $S_p$, then an image scan is initiated 82. Alternatively, if predicted subsequent contrast agent uptake measurement, $M_{Supp1}$, does not satisfy scanning parameter $S_p$, then another prep scan is performed 72.

Scanning parameter $S_p$, in accordance with one embodiment, is a scanning threshold, Th. Scanning threshold, Th, typically is selected to be representative of the contrast agent uptake peak with a selected range of tolerance. If predicted subsequent contrast agent uptake measurement, $M_{Supp1}$, meets or exceeds threshold, Th, then an image scan is initiated 82. That is, after a scan delay 84 to allow for positioning of the patient and for the patient to initiate a breath hold, a helical scan is performed 86. Since scan delay 84 is approximately the same as period of time, t, the image scan is performed 86 at approximately about the same time the actual contrast agent uptake reaches threshold, Th.

However, if subsequent contrast agent uptake measurement, $M_{Supp1}$, does not meet or exceed threshold, Th, then another prep scan is performed 72. As a result, a second base contrast agent uptake measurement, $M_{B2}$, is determined 74. The predictive algorithm is then applied 78 to at least one of the base contrast agent uptake measurements, $M_{B1}$, and $M_{B2}$, to predict 76 a new subsequent contrast agent uptake measurement, $M_{Supp2}$. Specifically, in one embodiment, second uptake measurement $M_{B2}$ is compared to first predicted subsequent uptake measurement $M_{Supp1}$, and base contrast agent uptake measurements, $M_{B1}$ and $M_{B2}$ are both used to modify the parameters of the predictive algorithm to predict second uptake measurement $M_{Supp2}$. The predictive algorithm therefore is dynamically adjusted in response to new base measurement, $M_{B2}$. The above referenced predictive algorithm provides for such dynamic adjustment.

Second predicted subsequent uptake measurement $M_{Supp2}$ is then compared 80 to scanning threshold, Th. If second subsequent contrast agent uptake measurement, $M_{Supp2}$, meets or exceeds threshold, Th, then the image scan is initiated 82. However, if second subsequent contrast agent uptake measurement, $M_{Supp2}$, does not meet or exceed threshold, Th, then yet another prep scan is performed 72 to determine 74 a third base contrast agent uptake measurement, $M_{B3}$. At least one of the measured base contrast agent uptake measurements, $M_{B1}$, $M_{B2}$, and $M_{B3}$, is then used to predict 76 yet another subsequent contrast agent uptake measurement, $M_{Supp3}$, which is compared 80 to scanning threshold, Th.

If subsequent contrast agent uptake measurement, $M_{Supp3}$, does not meet or exceed threshold, Th, then a prep scan is performed 72 to determine 74 base contrast agent uptake measurements, $M_{B4}$–$M_{BN}$, which are used to predict subsequent contrast agent uptake measurements, $M_{Supp4}$–$M_{SuppN}$, until subsequent contrast agent uptake measurement, $M_{SuppN}$, meets or exceeds threshold, Th. While the predictive algorithm described above utilizes at least one of each uptake measurement $M_{B1}$–$M_{BN}$, to predict subsequent contrast agent uptake measurements, $M_{Supp1}$–$M_{SuppN}$, the predictive algorithm may be modified. For example, the algorithm may be modified to use each uptake measurement $M_{B1}$–$M_{BN}$, to predict subsequent contrast agent uptake measurements, $M_{Supp1}$–$M_{SuppN}$. Similarly, the algorithm may be modified to use only one uptake measurement, $M_{B1}$–$M_{BN}$, to predict subsequent contrast agent uptake measurements, $M_{Supp1}$–$M_{SuppN}$. Furthermore, as explained above, the algorithm may be modified to include physiological characteristics of patient 22 and the contrast agent as parameters thereof.

Values for time, t, and threshold, Th, are selected, for example, prior to administering the contrast agent to patient 22, and stored, for example, in mass storage 38. Computer 36 can be configured to prompt the operator to input, or select, such values at operator console 40.

The above-described system substantially overcomes the difficulties associated with performing a scan during peak contrast agent uptake due to CT system scanning delays, and facilitates performing image scans during peak contrast agent uptake. In addition, the system is inexpensive to implement in known CT systems.

In accordance with another embodiment of the present invention, and rather than initiating a scan only when scanning threshold Th is reached, a scan can also be initiated when contrast agent uptake measurements either level off or decline. Particularly, if predicted contrast agent uptake measurement $M_{Supp1}$ is greater than scanning parameter $S_p$, then contrast agent uptake levels are increasing, and if measurement $M_{Supp1}$ is less than threshold Th, another prep scan is performed to determine a second base contrast agent uptake measurement $M_{B2}$. Scanning parameter $S_p$ is modified to have the same value as determined uptake measurement $M_{B2}$, and a subsequent base contrast agent uptake measurement $M_{Supp2}$ then is predicted and compared to scanning parameter $S_p$. Prep scans are performed, and scanning parameter $S_p$ is modified, until a predicted subsequent base contrast agent uptake measurement $M_{Supp2}$–$M_{SuppN}$ is equal to or less than scanning parameter $S_p$, or until an uptake measurement $M_{Supp2}$–$M_{SuppN}$ is equal to or greater than threshold Th.

When a predicted subsequent base contrast agent uptake measurement $M_{Supp1}$–$M_{SuppN}$ is equal to or less than scanning parameter $S_p$, i.e., when uptake measurement $M_{Supp1}$–$M_{SuppN}$ is equal to or less than respective base uptake measurement, $M_{B1}$–$M_{BN}$, then contrast agent uptake levels are leveling off or decreasing. Accordingly, if a predicted uptake measurement $M_{Supp1}$–$M_{SuppN}$ is equal to or less than scanning parameter $S_p$, and even if such predicted uptake measurement $M_{Supp1}$–$M_{SuppN}$ is less than threshold Th, then an image scan is initiated so that the image scan is performed during the contrast agent uptake peak.

Scanning parameter $S_p$ may be stored, for example, in mass storage 38. Scanning parameter $S_p$ may be updated, for example, by a processor (not shown) in computer 36. Alternatively, computer 36 may be configured to prompt the operator to input, or select, such parameter values at operator console 40.

In yet another embodiment, and rather than determining only one base measurement, a plurality of base measurements are determined. As is known, contrast agent uptake levels may differ between different regions of the same organ of patient 22. Accordingly, after patient 22 has been injected with a contrast agent, a prep scan is performed to determine base contrast measurements $M_{B1}$ and $M_{B2}$ for two regions of interest $ROI_1$ and $ROI_2$ of patient 22. Regions of interest $ROI_1$ and $ROI_2$ of patient 22 may be selected prior to the prep scan. Subsequent contrast agent uptake measurements, $M_{Supp1}$ and $M_{Supp2}$, are then predicted utilizing the predictive algorithm described above. The predicted subsequent contrast agent uptake measurements, $M_{Supp1}$ and $M_{Supp2}$, are then compared to a scanning parameter, $S_p$, such as a scanning threshold or the determined base measurements, to determine whether to initiate a scan, as described above. If each measurement, $M_{Supp1}$ and $M_{Supp2}$, satisfies scanning parameter $S_p$, i.e., meets or exceeds a scanning threshold, then a scan is initiated. Conversely, if neither measurement, $M_{Supp1}$ and $M_{Supp2}$, satisfies scanning parameter $S_p$, then new base measurements $M_{B3}$ and $M_{B4}$ are determined as described above. New subsequent measurements $M_{Supp3}$ and $M_{Supp4}$, are then predicted, as described above, and compared to scanning parameter $S_p$. Of course, a scan also can be initiated if contrast agent uptake levels are declining, as described above.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the CT system described herein is a "third generation" system, many other systems, such as "fourth generation" systems may be used. In addition, the algorithm described herein was implemented in connection with a helical scan, however the algorithm may also be implemented in connection with an axial scan. Accordingly, the spirit and scope of the invention are to be limited only by the terms of the appended claims.

What is claimed is:

1. A method for performing a tomographic scan of an object of interest injected with a contrast agent, said method comprising the steps of:
   (a) performing a prep scan of the object to determine at least one base contrast agent uptake measurement; and
   (b) predicting at least one subsequent contrast agent uptake measurement using a predictive algorithm and the determined base contrast uptake measurement.

2. A method in accordance with claim 1 further comprising the step of performing an image scan if at least one of the predicted subsequent contrast agent uptake measurement satisfies a scanning parameter.

3. A method in accordance with claim 1 further comprising the step of repeating steps (a) and (b) if the predicted subsequent contrast agent uptake measurement does not satisfy a scanning parameter.

4. A method in accordance with claim 1 wherein if at least one of the predicted subsequent contrast agent uptake measurements does not satisfy a scanning parameter, said method further comprises the steps of:
   (c) performing an additional prep scan of the object to determine at least one additional base contrast agent uptake measurement; and
   (d) predicting at least one subsequent contrast agent uptake measurement using the predictive algorithm and at least one of the determined base contrast uptake measurements.

5. A method in accordance with claim 4 wherein predicting at least one subsequent contrast agent uptake measurement using the predictive algorithm and at least one of the determined base contrast uptake measurements comprises the step of applying the predictive algorithm to each of the determined base contrast uptake measurements.

6. A method in accordance with claim 4 further comprising the step of performing an image scan if at least one of the predicted subsequent contrast agent uptake measurement satisfies a scanning parameter.

7. A method in accordance with claim 4 further comprising the step of repeating steps (c) and (d) if the predicted subsequent contrast agent uptake measurement does not satisfy a scanning parameter.

8. A system for performing a tomographic scan of an object of interest injected with a contrast agent, said system configured to:
   (a) perform a prep scan of the object to determine at least one base contrast agent uptake measurement; and
   (b) predict at least one subsequent contrast agent uptake measurement using a predictive algorithm and the determined base contrast uptake measurement.

9. A system in accordance with claim 8 further configured to perform an image scan if at least one of the predicted subsequent contrast agent uptake measurement satisfies a scanning parameter.

10. A system in accordance with claim 9 further configured to repeat steps (a) and (b) if at least one of the predicted subsequent contrast agent uptake measurement does not satisfy a scanning parameter.

11. A system in accordance with claim 8 wherein if at least one of the predicted subsequent contrast agent uptake measurements does not satisfy a scanning parameter, said system is further configured to:
    (c) perform an additional prep scan of the object to determine at least one additional base contrast agent uptake measurement; and
    (d) predict at least one subsequent contrast agent uptake measurement using a predictive algorithm and at least one of the determined base contrast uptake measurements.

12. A system in accordance with claim 11 wherein to predict at least one subsequent contrast agent uptake measurement using a predictive algorithm and at least one of the determined base contrast uptake measurements, said system is further configured to apply the predictive algorithm to each of the determined base contrast uptake measurements.

13. A system in accordance with claim 11 further configured to perform an image scan if the predicted subsequent contrast agent uptake measurement satisfies a scanning parameter.

14. A system in accordance with claim 11 further configured to repeat steps (c) and (d) if the predicted subsequent contrast agent uptake measurement does not satisfy a scanning parameter.

15. A system for producing a tomographic image of an object from scan data of the object, said system comprising an x-ray source and a detector, said object injected with a contrast agent, and said system configured to:
    (a) perform a prep scan of the object to determine at least one base contrast agent uptake measurement; and
    (b) predict at least one subsequent contrast agent uptake measurement using a predictive algorithm and the determined base contrast uptake measurement.

16. A system in accordance with claim 15 further configured to perform an image scan if the predicted subsequent contrast agent uptake measurement satisfies a scanning threshold.

* * * * *